United States Patent [19]
Lim et al.

[11] Patent Number: 4,743,851
[45] Date of Patent: May 10, 1988

[54] APPARATUS AND METHOD FOR CREATING NON-ORTHOGONAL MAGNETIC RESONANCE IMAGING

[75] Inventors: Arthur J. Lim, Menlo Park; Michael H. Buonocore, Redwood City; Craig H. Barratt, Mountain View, all of Calif.

[73] Assignee: Resonex, Inc., Sunnyvale, Calif.

[21] Appl. No.: 89,941

[22] Filed: Aug. 25, 1987

Related U.S. Application Data

[63] Continuation of Ser. No. 769,939, Aug. 27, 1985, abandoned.

[51] Int. Cl.⁴ ............................................. G01R 33/20
[52] U.S. Cl. .................................... 324/309; 324/312
[58] Field of Search ................ 364/414, 487; 324/300, 324/307, 309, 312, 313, 318, 322; 128/653

[56] References Cited

U.S. PATENT DOCUMENTS

| | | | |
|---|---|---|---|
| 4,284,948 | 8/1981 | Young | 324/309 |
| 4,300,096 | 11/1981 | Harrison et al. | 324/309 |
| 4,322,684 | 3/1982 | Hounsfield | 324/309 |
| 4,333,053 | 6/1982 | Harrison et al. | 324/309 |
| 4,510,448 | 4/1985 | Riedl | 324/309 |
| 4,573,015 | 2/1986 | Abe et al. | 324/309 |
| 4,585,995 | 4/1986 | Flugan | 324/322 |
| 4,599,565 | 7/1986 | Hoenninger, III et al. | 324/309 |
| 4,625,171 | 11/1986 | Sekihara et al. | 324/312 |
| 4,649,347 | 3/1987 | Hwang et al. | 324/309 |

*Primary Examiner*—Michael J. Tokar
*Attorney, Agent, or Firm*—Flehr, Hohbach, Test, Albritton & Herbert

[57] ABSTRACT

In an improved NMR imaging method for forming images of a subject by determining the relative densities of nuclei within the subject, three orthogonal gradient fields are generated by digitally storing three gradient waveforms for each orthogonal direction, with each waveform being individually compensated and calibrated with respect to an axis with which it is associated. Nine associated matrix multiplying functions which determine the coordinates of a desired slice in its rotated plane are also stored by an external input (by computer or by the clinician operating the system.) Then, in a sequential fashion, digital words for each gradient waveform are read out, multiplied by pairs with the appropriate multiplying function and the three terms are added to form a digital word. These words are converted to an analog value and applied to the respective gradient coils.

17 Claims, 4 Drawing Sheets

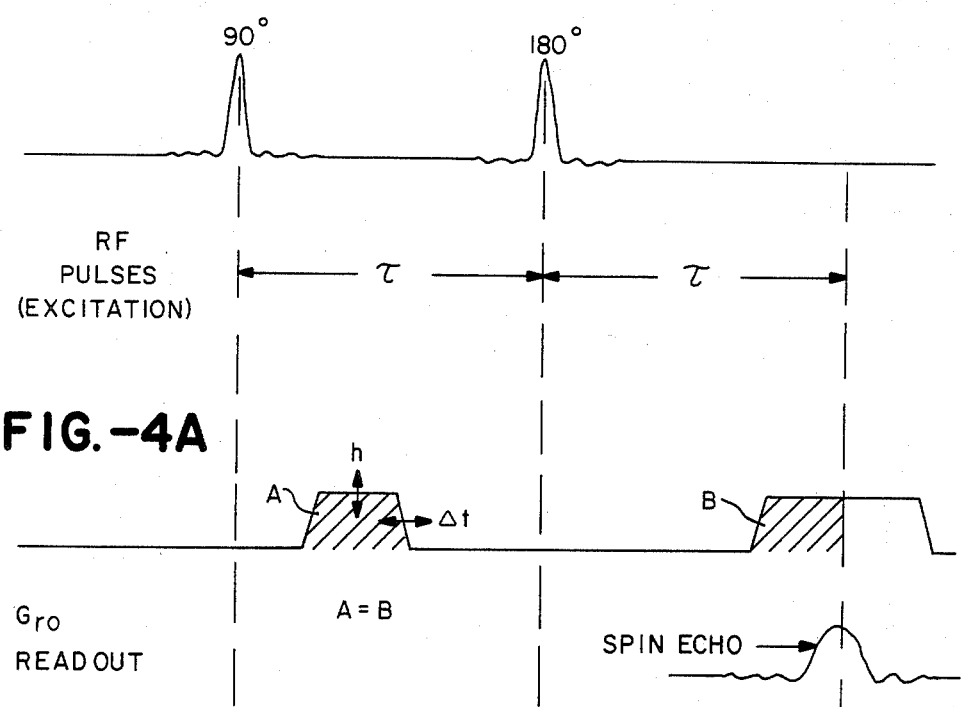
FIG.-4A
FIG.-4B
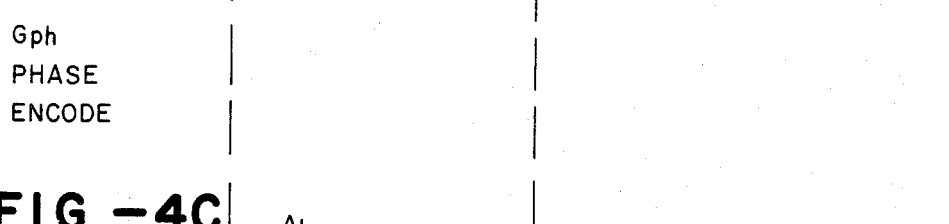
FIG.-4C
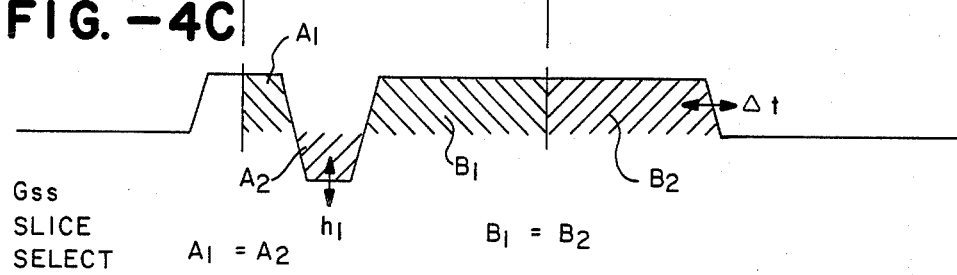
FIG.-4D

FIG.—5A
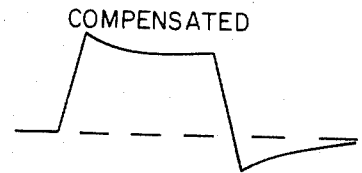
FIG.—5B
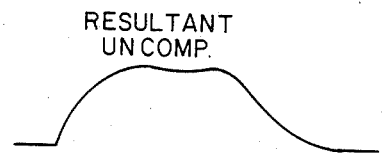
FIG.—5C
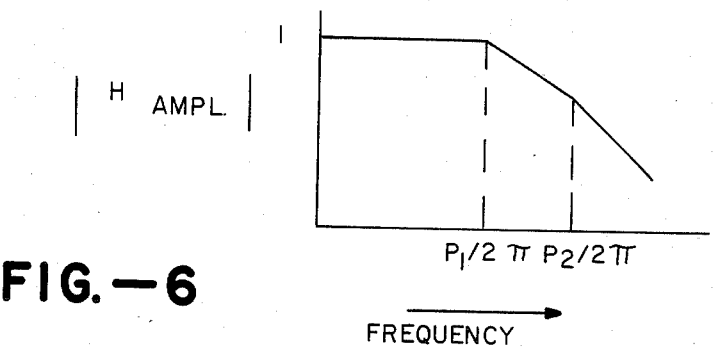
FIG.—6
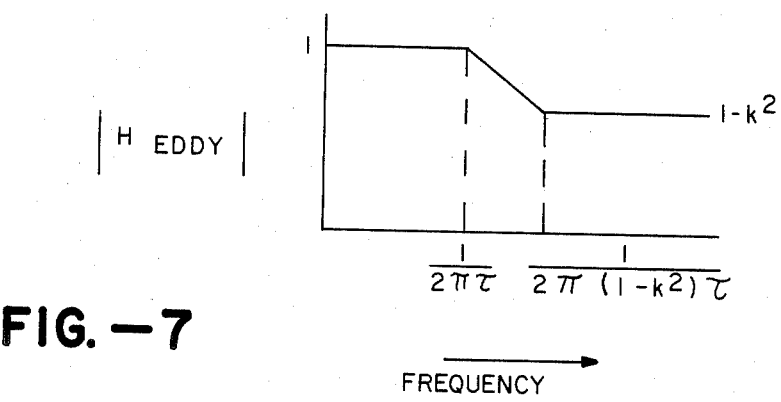
FIG.—7

APPARATUS AND METHOD FOR CREATING NON-ORTHOGONAL MAGNETIC RESONANCE IMAGING

This is a continuation of application Ser. No. 769,939, filed Aug. 27, 1985, and now abandoned.

FIELD OF THE INVENTION

This invention relates to an imaging apparatus and method for magnetic resonance and more particularly to an apparatus and method for generating non-orthogonal gradient voltages. The use of nuclear magnetic resonance techniques for non-invasive examinations of a body (human or inanimate) is now becoming well established. U.S. Pat. No. 4,297,637 with Crooks, et al., as inventor, illustrates one NMR imaging technique and also discloses a large list of pertinent patents and other publications relating to magnetic resonance imaging.

BACKGROUND OF THE INVENTION

One difficulty with present magnetic resonance imaging techniques and systems is that the image is limited to orthogonal planes. This means that the image plane can only be made parallel to the faces of a cube. In order to fully realize the capabilities of magnetic resonance imaging, it is necessary to create an image at any arbitrary orientation. Theoretically, as discussed in the General Electric booklet entitled: *NMR: A Perspective on Imaging*, published in 1982 by the General Electric Company Medical Systems Operations of Milwaukee, Wis., by adjustment of the gradient system which produces the spatial linear field gradients crucial to NMR imaging, a "tilted gradient" may be provided. The General Electric booklet states that this is implemented by "suitably combining two or all three gradients."

However, it has not been practical to obtain an image of an arbitrary angular orientation, because of non-idealities in the NMR system. For example, in a heart scan it might be desirable to make images of the outer surface of the heart at different angles. With present NMR techniques this is not possible.

OBJECTS AND SUMMARY OF THE INVENTION

It is an object of the present invention to provide an improved magnetic resonance imaging apparatus and method.

It is a more detailed object of the present invention to provide an apparatus and method as above in which an image of any arbitrary orientation may be provided in a clinical environment.

In accordance with the above objects, the present invention is directed to an apparatus and method for generating gradient waveforms for a plurality of orthogonal axes for driving the gradient coils of a magnetic resonance imaging apparatus to provide a selected image of a subject. It includes the steps of providing a plurality of matrix multiplying functions with each being associated with a gradient coil for forming a matrix which is a function of the orientation of the image. With the foregoing matrix multiplying functions the image is capable of being rotated in at least two orthogonal directions by variation of the matrix functions. For a particular magnetic resonance apparatus for each matrix multiplying function, there is provided an associated gradient waveform which is corrected for non-idealities in the apparatus. The corrected gradient waveforms are converted into a digital format and digitally stored.

An electrical signal for driving a selected gradient coil by multiplying matrix functions associated with the coil with its associated stored waveform and adding the products.

BRIEF DESCRIPTION OF THE DRAWINGS

FIG. 4A shows RF excitation pulses.

FIGS. 4B, 4C and 4D show related gradient waveforms.

FIGS. 5A, 5B and 5C are various gradient waveforms.

FIG. 6 is a characteristic curve useful in understanding the invention.

FIG. 7 is a characteristic curve useful in understanding the invention.

DETAILED DESCRIPTION OF THE INVENTION

Figure 1:
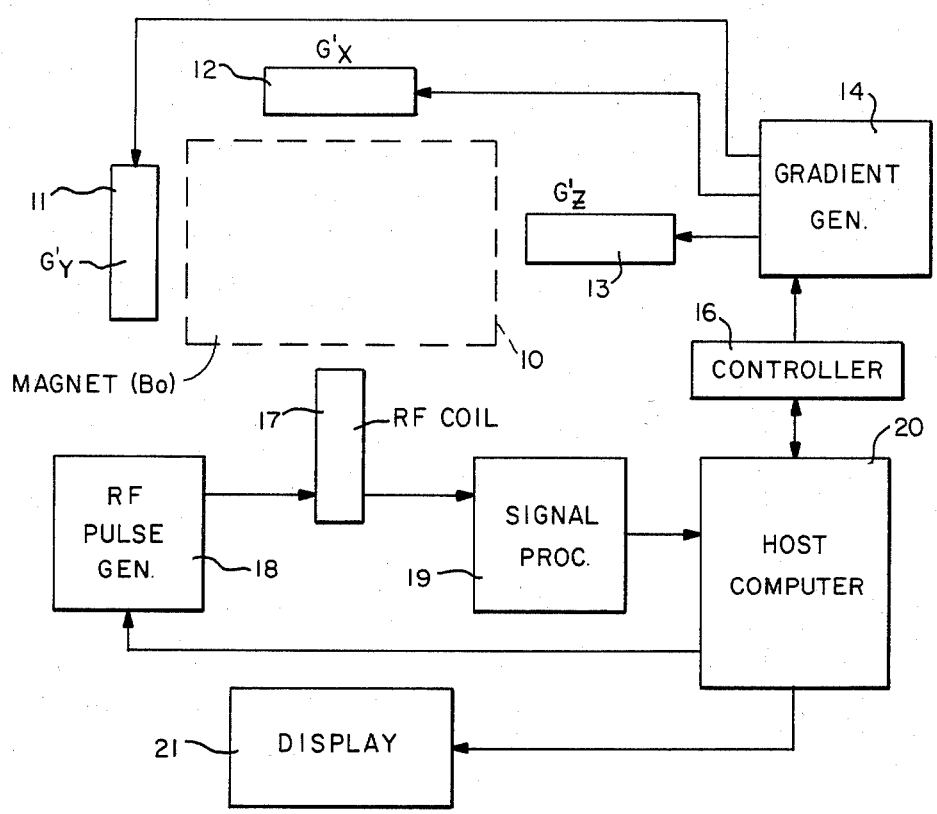
FIG. 1 is a block diagram of an NMR system embodying the present invention.

FIG. 1 illustrates an NMR system which in its block diagram form is of a standard type. However, with the process of the present invention and detailed circuitry shown in FIG. 2, it is possible to practice the improved method of the present invention.

Referring specifically to FIG. 1, the main magnet 10 provides a magnetic field B0 which generates a static magnetic field realizing a polarization of the nuclei of the subject. Within magnet 10 therefore is a cavity or space in which the specimen or human to be examined is placed. Such main magnetic field can be generated by an electrically excited air core or iron core in which the conductor can be of a resistance-type formed of copper or aluminum or a superconducting conductor which is cryogenically cooled. In addition, it can be a permanent magnet. Typically, the main magnet provides a linear uniform field about the subject. It should be noted that, in the case of a human being, because of space limitations, orientation of the human within the confines of the main magnet 10 is often severely restricted from a practical standpoint to one direction only; in other words the body cannot be shifted to obtain a desired angular orientation.

The apparatus also includes a gradient system utilized for producing spatial linear field gradients. These gradient fields are conventionally established by the use of a set of three orthogonal direct current coils which generate the three principle gradients, $G'_x$, $G'_y$ and $G'_z$. The coils themselves are numbered 11 through 13, and are driven by a gradient generator 14, which in turn is controlled by a controller 16 which in turn communicates with a host computer 20.

Finally, the third component of the typical NMR system includes the radio frequency (RF) coil 17, which is used for generating radio frequency fields in the subject being analyzed and for picking up the free induction decay or spin echo signal which is generated after termination of the ratio frequency pulse. The RF coil may be a single coil which serves for both excitation and detection, or alternately separate transmitter and receiver coils. Exciting the RF coil 17 is an RF pulse unit 18 which generates a highly stable radio frequency output. The signal processor 19 receives the small microvoltage level spin echo signals generated by the subject and these are processed by computer 20 to form an image. Generally the image is digitized in an analog to digital converter and stored in the memory section of computer 20 for later display by means of a display 21 hich may typically be a cathode ray tube. In other words, computer 20 computes and generates a reconstructed image of the subject in terms of individual pixel values which can be displayed on the cathode ray tube.

Figure 2:
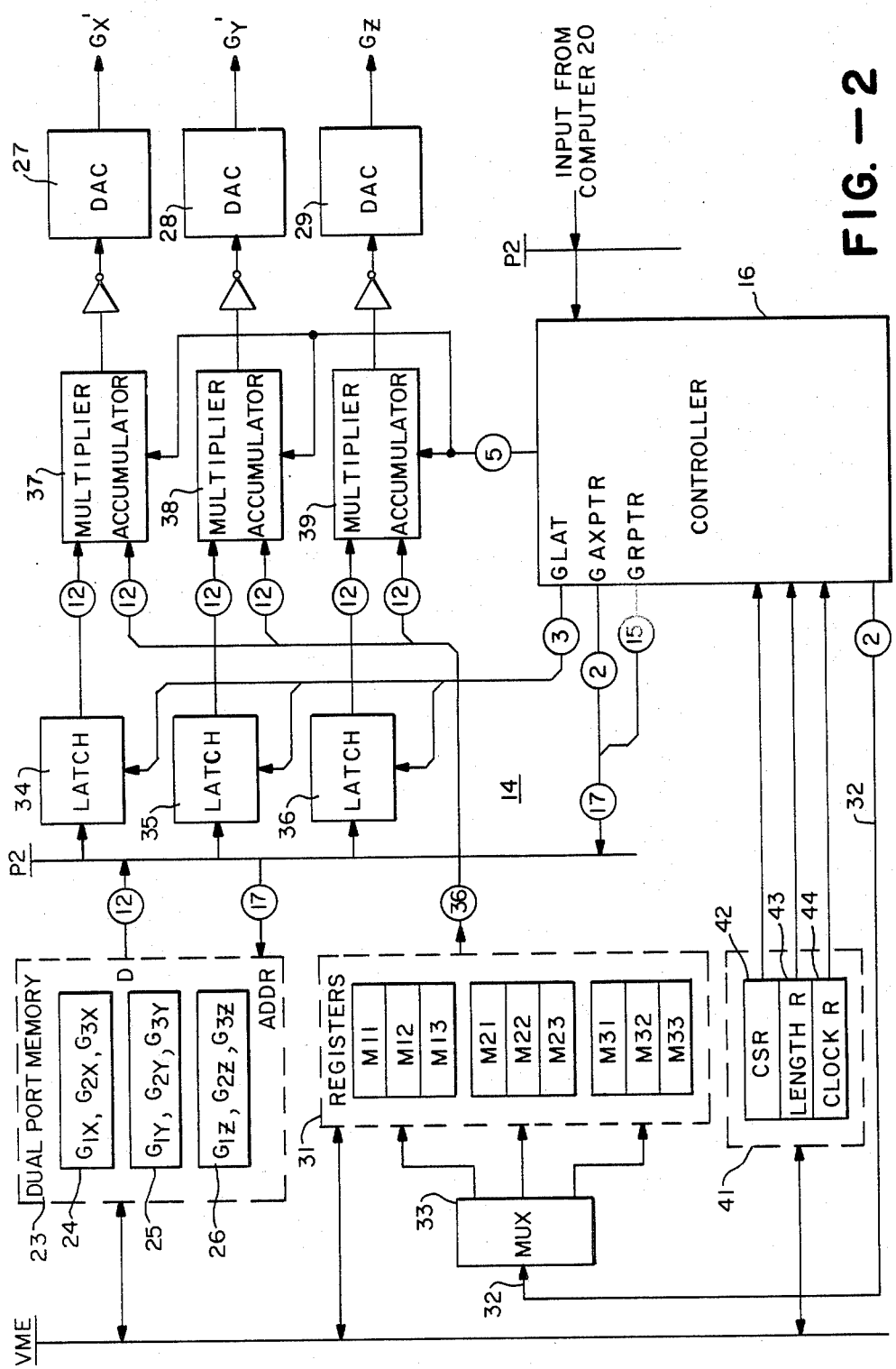
FIG. 2 is a more detailed circuit schematic of a portion of FIG. 1.

Referring now to FIG. 2, there is illustrated the controller 16 and the gradient generator 14. Referring specifically to the gradient generator, a dual port memory 23 includes the individual orthogonal gradient memories 24, 25 and 26 corresponding to $G'_x$, $G'_y$ and $G'_z$, respectively. Here, appropriate gradient waveforms are digitally stored. As will be discussed in detail below, they are reconstructed in a specific manner and converted by the digital to analog converters 27, 28 and 29 to analog waveforms or electrical signals designated $G'_x$, $G'_y$ and $G'_z$ which drive the coils 11, 12 and 13 of FIG. 1. The prime indicates a rotated set of axes relative to X, Y and Z orthogonal axes.

Figure 3:
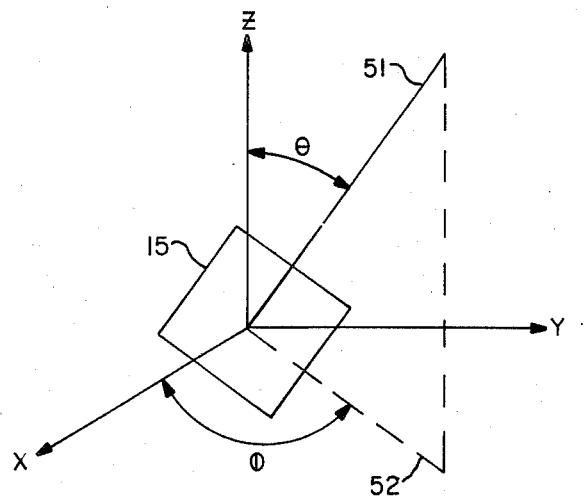
FIG. 3 is a three-dimensional axis system illustrating the angular conventions used in the present application.

In a typical application the present invention provides an image in the form of a "slice" which has a particular orientation. FIG. 3 defines the orientation angles used here. A selected slice is shown as 15 in the drawing. Its orientation is defined by a line 51 which is normal to this slice. The angle theta ($\theta$) is then the tilt of the normal from the Z axis. From line 51, there is a projection indicated as line 52 of this normal into the XY plane. Then the angle phi ($\phi$) is the rotation of this projected normal away from the X axis. Thus, the two angle, theta and phi, determine the orientation of the slice.

For convenience of viewing, a third angle omega ($\Omega$) is required to specify the orientation of the image within the selected slice. This angle is generally either zero degrees or 90 degrees. In other words this is like tilting a photograph on its side. In an NMR imaging system, theta and phi, can be chosen by the operator; omega may then be always taken to be zero degrees or can be chosen on the basis that the longness dimension of the image of the subject appears horizontally on the image display. A more detailed and methematical discussion of the foregoing orientation will be given below.

The present invention is best utilized with a spin echo signal rather than free induction decay. (This is because of the greater time delay between activating signals.) A typical imaging sequence, in order to form an image, is illustrated in FIGS. 4A through 4D. FIG. 4A shows the 15 typical RF pulses and excitation signals for 90 degrees and 180 degrees with a time interval between the two signals of tau ($\tau$).

As illustrated in FIGS. 4B, 4C and 4D, three basic waveforms may be needed; these might be a readout waveform, Gro, as illustrated in FIG. 4B, a phase encoding waveform, Gph, in FIG. 4C; and a slice select waveform, $G_{ss}$, FIG. 4D.

As illustrated by FIG. 4B, the readout waveform, the spin echo signal occurs at a time two Tau ($\tau$). This process of refocusing by use of a 180° pulse to produce the spin echo is well known. Because of non-idealities in the system (such as, eddy current and amplifier effects which will be discussed below) the echo may not occur at the desired time. The possible reasons for this are that first the bandwidth of amplifiers that drive the gradient coils are finite; and secondly switching currents in the gradient coils will induce eddy currents in the yoke of the main magnet. These eddy currents will produce fields that tend to counteract the gradient fields. Thus, the actual echo time may be shifted from the desired echo time. Two solutions which have been utilized for calibration in the past is to either change the height, h, of the A pulse so that area A equals the area B, where the area B is ½ of the total waveform so that the spin echo falls in the midline of that waveform.

Similarly, for the slice select function of FIG. 4D, an adjustment in height, $h_1$ is made so that the area A2 is equal to A1 and the pulse width $\Delta t$, is adjusted so that the area B2 is made equal to area B1.

It should be emphasized that the imaging sequence shown above in FIGS. 4B, 4C and 4D is only one type of imaging sequence and this sequence is one that will produce a slice at a selected orientation. However, where for example, volume imaging is done, then perhaps just the readout gradient waveform and a pair of phase encode waveforms are necessary.

In a typical prior art NMR imaging systems, the waveforms FIGS. 4B, 4C and 4D would be converted to appropriate voltage values and applied directly to the X,Y and Z gradient coils, respectively. (See equations 19, 20 and 21.) As discussed above, the image is thus limited to orthogonal planes with the image plane being made parallel to one of the faces of a cube defined by X, Y and Z orthogonal axes.

In accordance with the invention, for a selected arbitrary image orientation a 3×3 matrix is defined as shown by equations 1, 2 and 3. Here the "M" values define the matrix multiplying functions which provide the orientation of the image related to values of the angles, phi, theta and omega, and the "G" functions are corrected gradient waveforms, which are related to those of FIGS. 4B, 4C and 4D. For example, readout, phase encoding and slice select, as specifically shown in equations 4, 5 and 6. In other words, associated with each of the rotation matrix coefficients "M", there is a specific gradient waveform. Equations 1, 2 and 3 are in essence a superset of equations, compared to the orthogonal subset, 19, 20 and 21, which changes the reference of the coordinate system, in that non-orthogonal images may be provided. This is especially useful, for example, where one may wish to align the Z axis with various surfaces of the heart. It has been found that because of non-idealities in the NMR system (and for that matter one particular NMR apparatus will vary from another) the use of a single set of gradient waveforms, such as illustrated in FIGS. 4B, 4C and 4D is not sufficient. Rather as illustrated in equations 1, 2 and 3, a gradient waveform related to each matrix function must be provided. This means that, for example, referring to equations 1 and 4, that the gradient waveforms $G_{1x}$, $G_{2x}$ and $G_{3x}$ are related to a readout gradient waveform for the X axis and a phase encode waveform for the X axis and a slice select waveform for the X axis. The same is true of the other nominal orthogonal axes which for convenience relate to the respective gradient coils. It should be mentioned that the gradient coils are typically arranged along the orthogonal axes. Of course, they could be arranged with unique and arbitrary axes so that the X, Y and Z need not necessarily be mathematically orthogonal. However, this would, of course, result in increased computational complexity.

Thus, as is apparent from equations 4, 5 and 6, in a typical application a minimum of nine matrix functions are necessary along with nine associated and different gradient waveforms. This is for full flexibility and orientation.

Where it is acceptable to, for example, have one plane parallel to one axis, a smaller matrix as illustrated by equations 22, 23 and 24 may be utilized. Here the $G_Z$ gradient includes only one term with $G_x$ and $G_y$ having two terms.

This is the situation where the angles theta and omega are zero. Equation 25 illustrates the theoretical matrix with the phi angle being a parameter.

Briefly referring to the rotation matrix coefficients M, and their relationship with the angles as discussed in FIG. 3, phi and theta, and also omega, equations 10 through 18 define the various M-factors. The M-factors as illustrated by equations 7, 8 and 9, are shown as primed since the M-factors as defined by equations 10 through 18 are actually multiplied or adjusted by various K-factors. Specifically, the phase and readout strengths determine the resolution of the final image and $K_{ss}$ the slice select strength, determine thickness.

The basic matrix "M" values must be computed for each selected set of theta and phi values. This can be done by the computer 20, by appropriately utilizing previously computed and stored values for immediate recall. Alternatively, the values could be generated by the computer simply in response to a manual selection by either a keyboard or a joystick input. For convenience of the user, the same conventions are used as in conventional x-ray angiography.

As discussed above, because of non-idealities in the NMR system, it has been found that a gradient waveform for each matrix factor multiplying function must be provided. This is done on site with a particular NMR apparatus. In other words, in one typical situation, for example, the $G_{ro}$ gradient waveform of FIG. 4B would be applied successively to the gradient coils, that is the nominally X, Y and Z gradient coil of the apparatus. The calibration correction is already indicated in FIG. 4B, where the A area would be adjusted equal to B area. However, initially a compensation correction should be made which compensates for the smoothing effect caused by roll off of associated amplifiers and also for eddy currents effects.

As indicated in the sequence of FIGS. 5A, 5B and 5C, FIG. 5A is the desired gradient pulse as applied which in effect forms a gradient field of the same waveshape. However, because of the eddy current and bandwidth effects, the actual waveform might be FIG. 5C. In the prior art, calibrations are described in conjunction with FIG. 4B, where the pulse height or width is adjusted which results in some partial correction. But for a total correction an inverse transfer function as set out in FIG. 5B must be used. In effect, a digital filter in, for example, the controller 16, or the computer 20 would provide this compensation which effectively provides the distorted waveform of FIG. 5B.

In general since the gradient fields are much smaller than the main field, Bo, the effect of the eddy currents will be very close to linear. Also, with respect to the amplifier roll off (that is of the amplifier which amplifies the electrical signal applied to the gradient coil), it will also be linear. Thus, if the gradient system is linear, it is possible to measure the frequency responses of the components of the gradient system.

As illustrated in FIG. 6, a typical frequency response of the gradient amplifier is as shown where there are two pole frequencies so indicated. Equation 26 is the functional form of the amplifier roll-off effect. With respect to eddy currents, FIG. 7 shows a typical response. The functional form of the eddy current effect is set out in equation 27. Equation 28 shows the filter function, a compensation function G(s) which would be placed in the computer 20 which is the inverse of the product of the amplifier transfer function and the eddy current transfer function. The foregoing correction as illustrated in FIG. 5B is especially useful in an electromagnet type of NMR apparatus as opposed to superconducting magnets where the time constants are much longer and thus more difficult to compensate for.

Another technique for compensating, is by a direct measurement of the gradient system by applying a subset of frequencies to it. Here the amplitude and phase response of the system is measured by a coil placed in the magnetic field, the coil giving a readout as shown in the equation 29. Here the subscript "i" is the sequence, 0,1,n of the frequency subset. Then the compensating filter data can be interpolated to establish the value of "G" for all values of "f" and stored in software in computer 20.

Either of the foregoing techniques or a combination of the two can be utilized on-site and then stored in computer 20. And as discussed above, after such compensation the calibration techniques as described in conjunction with FIGS. 4B and 4D, are utilized. Phase encode as shown in FIG. 4C does not require calibration.

Thus the desired gradient waveform values for each matrix multiplier in accordance with equations 1, 2 and 3, is stored as indicated in memories 24, 25 and 26. These values are in effect universal constants which are effective for any selected orientation or rotation of an image. This is true since the various waveforms have been compensated with respect to each of the three relative orthogonal axes. Again this is necessary because of the non-idealities of the system.

The "M" matrix functions are stored in register units 31 (FIG. 2). As discussed above these are either prestored in the computer 20 or generated by manual inputs. Then the controller 16 via the output line 32 which drives the multiplexer 33 stores the M values. Thus controller 16 may, for example, in a scan mode take oblique pictures at 1° angle increments over 2-pi radians. Multiplier accumulators 37, 38 and 39 under the direction of controller 16 multiply the appropriate M-factor with the appropriate G-factor as expressed in equations 1, 2 and 3. This is in effect a pairwise vector multiplication and then a summation (accumulation) of these terms. Such summation is a digital word which when converted by digital to analog converters 27, 28 and 29 forms a segment of the analog gradient waveform. Finally, under the control of the controller in a sequential fashion, each additional word containing in effect a sample or another segment of the analog gradient waveform is converted to analog by the associated converters 27, 28 and 29. In this manner, a full-corrected on-line electrical signal is provided which, when combined with the other two gradient voltages, provide for immediate selection of an image of arbitrary slice orientation.

Thus to momentarily summarize, the component factors of the equations 1, 2 and 3 have been stored in order to execute the equations, and the latches 34, 35 and 36 under the control of controller 16 supply the appropriate gradient waveform to the associated multiplier accumulators 37, 38 and 39, which are all under the control of controller 16.

In order to control the rate at which the waveforms are clocked out and the length of the waveforms, additional control registers 41 are provided, which include the control status register 42, length register 43 and the clock register 44 which determines how fast the waveforms are clocked out.

Thus, a very fast on line NMR imaging apparatus is provided in which an image of any arbitrary angular orientation can be immediately selected in a clinical environment. This is partially due to the realization that the gradient waveform is dependent on the non-idealities of a particular NMR system. And then as is apparent from equations 1, 2 and 3 in effect universal constants are generated on site (which will be effective for a long period of time unless some mechanical parameter of the apparatus changes) to allow any slice orientation to be utilized. The use of digital computer techniques, where the waveforms are digitally stored and then read out and converted on site to an analog waveform, provide an effective method of producing an accurate analog voltage waveform allowing for successive changes of orientation at a very fast rate.

$$G'_x = M'_{11} G_{1x} + M'_{12} G_{2x} + M'_{13} G_{3x} \tag{1}$$

$$G'_y = M'_{21} G_{1y} + M'_{22} G_{2y} + M'_{23} G_{3y} \tag{2}$$

$$G'_z = M'_{31} G_{1z} + M'_{32} G_{2z} + M'_{33} G_{3z} \tag{3}$$

$$G_{1x} = G_{rox} \quad G_{2x} = G_{phx} \quad G_{3x} = G_{ssx} \tag{4}$$

$$G_{1y} = G_{roy} \quad G_{2y} = G_{phy} \quad G_{3y} = G_{ssy} \tag{5}$$

$$G_{1y} = G_{roz} \quad G_{2z} = G_{phz} \quad G_{3z} = G_{ssz} \tag{6}$$

$$M'_{11} = M_{11} K_{ro} \quad M'_{12} = M_{12} K_{ph} \quad M'_{13} = M_{13} K_{ss} \tag{7}$$

$$M'_{21} = M_{21} K_{ro} \quad M'_{22} = M_{22} K_{ph} \quad M'_{23} = M_{23} K_{ss} \tag{8}$$

$$M'_{31} = M_{31} K_{ro} \quad M'_{32} = M_{32} K_{ph} \quad M'_{33} = M_{33} K_{ss} \tag{9}$$

$$M_{11} = \cos \Omega \cos \phi \cos \theta - \sin \Omega \sin \phi \tag{10}$$

$$M_{12} = -\sin \Omega \cos \phi \cos \theta - \cos \Omega \sin \phi \tag{11}$$

$$M_{13} = \cos \phi \sin \theta \tag{12}$$

$$M_{21} = \cos \Omega \sin \phi \cos \theta + \sin \Omega \cos \phi \tag{13}$$

$$M_{22} = \cos \Omega \cos \phi - \sin \Omega \sin \phi \cos \theta \tag{14}$$

$$M_{23} = \sin \Omega \sin \theta \tag{15}$$

$$M_{31} = \cos \phi \sin \theta \tag{16}$$

$$M_{32} = \sin \phi \sin \theta \tag{17}$$

$$M_{33} = \cos \theta \tag{18}$$

Orthogonal Subset $$G'_x = M'_{13} G_{3x} \tag{19}$$

$$G'_y = M'_{22} G_{2y} \tag{20}$$

$$G'_z = M'_{31} G_{1z} \tag{21}$$

$$G'_x = M'_{11} G_{1x} + M'_{12} G_{2x} \tag{22}$$

$$G'_y = M'_{21} G_{1y} + M'_{22} G_{2y} \tag{23}$$

$$G'_z = 1 \, G_{3z} \tag{24}$$

where $\theta = 0, \Omega = 0$ $$M = \begin{matrix} \cos \phi & -\sin \phi & 0 \\ \sin \phi & \cos \phi & 0 \\ 0 & 0 & 1 \end{matrix} \tag{25}$$

$$H_{ampl}(s) = \frac{P_1 P_2}{(S + P_1)(S + P_2)} \tag{26}$$

where $s = j 2\pi f$ $$H_{eddy}(s) = \frac{(1 - k^2) \tau s + 1}{\tau s + 1} \tag{27}$$

$$G(s) = \frac{1}{H(s)} = \frac{1}{H_{ampl}(s) H_{eddy}(s)} \tag{28}$$

$$G(j 2\pi f_i) = A_i e^{j\phi_i} \tag{29}$$

where $A_i$ is the measured amplitude at frequency $f_i$,
$\phi_i$ is the measured phase at $f_i$.

What is claimed:

1. A method for generating gradient waveforms for a plurality of axes for driving the gradient coils of a magnetic resonance imaging apparatus to provide a selected image of a subject, each axis corresponding to the direction of a spatial linear field gradient produced by one of the gradient coils, comprising the following steps:

(a) providing a plurality of matrix multiplying functions, at least two of each of said matrix multiplying functions being associated with each of at least two gradient coils, for forming a matrix which is a function of the orientation of said image, said image being capable of being rotated at least in two orthogonal directions by variation of said matrix functions;

(b) for a particular magnetic resonance imaging apparatus for each axis associated with a gradient coil and said associated multiplying functions providing for each said multiplying function an associated gradient waveform corrected for non-idealities in said apparatus related to said axis of said gradient coil;

(c) storing each of said corrected gradient waveforms;

(d) providing an analog electrical signal for driving a selected gradient coil by multiplying said matrix functions associated with a said coil with said associated waveforms and (e) adding the products.

2. A method as in claim 1, wherein there are three orthogonal axes and three gradient coils and wherein said step of providing and forming a matrix, nine matrix multiplying functions are provided, three functions being associated with each gradient coil to form a matrix which is a function of phi ($\phi$) and theta ($\theta$) which determines the coordinates of a slice of said magnetic resonance imaging image and its rotated plane.

3. A method as in claim 1, wherein said correction of said gradient waveforms includes compensation for eddy current effects.

4. A method as in claim 1, wherein said correction of said gradient waveforms includes calibration for eddy current effects.

5. A method as in claim 3, where said compensation includes distorting said waveforms to counteract smoothing effects of said eddy currents.

6. A method as in claim 5, where said distortion is determined by a predicted transfer function of said gradient coil of a particular apparatus.

7. A method as in claim 1, including the step of controlling the length of said waveforms forming said electrical signal and the rate at which said waveform is digitally clocked out to said gradient coil.

8. A method as in claim 1, where in said step of providing said electrical signal said added products are converted from a digital format to an analog format.

9. A method as in claim 1, where said correction of said gradient waveforms includes in sequence compensation by distorting said wave forms to counteract the smoothing effects to eddy currents in the gradient coils and thereafter calibrating said waveforms.

10. A method as in claim 9 or claim 4, where said calibration includes the step of adjusting the pulse height or width of said gradient waveforms.

11. In a magnetic resonance imaging apparatus, x, y and z gradient coils, means for generating three different waveforms, multiplier means, means for distributing the three different waveforms to said multiplier means, accumulating means, means connecting the multiplier means to the accumulating means and means connecting the accumulating means to the x, y and z gradient coils whereby there can be applied to the gradient coils waveforms to make possible the selection of arbitrarily oriented image planes which can be rotated about axes perpendicular to the image planes.

12. Apparatus as in claim 11 wherein said means for distributing the waveforms includes latch means for controlling the timing of the application of the three different waveforms to the multiplier means.

13. Apparatus as in claim 11 wherein the accumulating means stores the waveforms in digital form and wherein said means for supplying the output accumulating means to the coils includes a digital to analog converter.

14. Apparatus as in claim 11, together with means for correcting for non-idealities in said apparatus related to the waveform supplied to each of said gradient coils.

15. In a magnetic resonance imaging apparatus, x, y and z gradient coils, means including multiplier means and accumulating means for supplying three analog waveforms to each of said gradient coils to provide selected arbitrarily oriented image planes which can be rotated about an axis perpendicular to the image planes.

16. Apparatus as in claim 15 wherein said means including multipliers and accumulating means includes means for selecting multiplication factors for the multipliers.

17. In a method for generating waveforms for driving the x, y and z gradient coils of a magnetic resonance imaging apparatus to provide an arbitrarily selected image of a subject being examined, generating three different waveforms, distributing the generated waveforms and multiplying the waveforms with multiplying functions to provide a multiplied output for each of the waveforms, accumulating the multiplied output of the waveforms and supplying the multiplied and accumulated outputs of the waveforms to the x, y and z coils to provide a selected arbitrarily oriented image plane which can be rotated about an axis perpendicular to the image plane.

* * * * *